(12) United States Patent
Hatcher et al.

(10) Patent No.: US 7,179,420 B2
(45) Date of Patent: Feb. 20, 2007

(54) APPARATUS COMPRISING A PARTICLE SORTER/DISPENSER AND METHOD THEREFOR

(75) Inventors: Thomas James Hatcher, Burlington Township, NJ (US); Ilya Feygin, Mountainside, NJ (US); Aleksandr Grinberg, Old Bridge, NJ (US); Joseph J. Brzezinski, Bangor, PA (US)

(73) Assignee: TechElan, LLC, Mountainside, NJ (US)

( * ) Notice: Subject to any disclaimer, the term of this patent is extended or adjusted under 35 U.S.C. 154(b) by 472 days.

(21) Appl. No.: 10/280,537

(22) Filed: Oct. 25, 2002

(65) Prior Publication Data

US 2003/0148531 A1 Aug. 7, 2003

Related U.S. Application Data

(60) Provisional application No. 60/343,830, filed on Oct. 25, 2001.

(51) Int. Cl.
*G01N 33/00* (2006.01)
*G01N 35/08* (2006.01)
(52) U.S. Cl. .................... 422/73; 422/68.1; 422/82.05; 422/100; 422/103; 436/63; 436/52; 436/164; 436/180
(58) Field of Classification Search ............... 422/68.1, 422/73, 82.05, 100, 101, 103; 436/63, 52, 436/54, 164, 177, 180; 435/4, 29, 287.1, 435/287.3
See application file for complete search history.

(56) References Cited

U.S. PATENT DOCUMENTS

| | | | | |
|---|---|---|---|---|
| 3,827,555 A | * | 8/1974 | Kamentsky et al. | 209/546 |
| 4,756,427 A | * | 7/1988 | Gohde et al. | 209/3.1 |
| 5,837,200 A | * | 11/1998 | Diessel et al. | 422/73 |
| 6,540,895 B1 | * | 4/2003 | Spence et al. | 204/450 |
| 6,778,724 B2 | * | 8/2004 | Wang et al. | 385/16 |
| 2003/0027225 A1 | * | 2/2003 | Wada et al. | 435/7.21 |

OTHER PUBLICATIONS

Hawley, G. The Condensed Chemical Dictionary, 10th edition, 1981, p. 1081.*

* cited by examiner

*Primary Examiner*—Maureen M. Wallenhorst
(74) *Attorney, Agent, or Firm*—DeMont & Breyer, LLC

(57) ABSTRACT

A particle sorter/dispenser wherein particles that are suspended in a liquid are flowed through a conduit and selectively dispensed through a dispensing orifice. The conduit includes a sensing zone wherein the liquid-suspended particles are interrogated by a sensor. Data from the sensor is received by processing electronics that analyzes the data from the sensor and makes a decision whether or not to dispense a particle. The particle sorter/dispenser further includes a switch that, responsive to a signal from the processing electronics, controls whether or not a given particle is dispensed through the dispensing orifice. The switch has one or two valves that introduce relatively high-pressure liquid into the conduit. The flow streamlines of the high-pressure liquid controls the flow of the relatively low-pressure liquid-suspended particles in the conduit. Particles that are not dispensed are flowed past the dispensing orifice to a recycle reservoir that depends from the downstream end of the conduit.

19 Claims, 6 Drawing Sheets

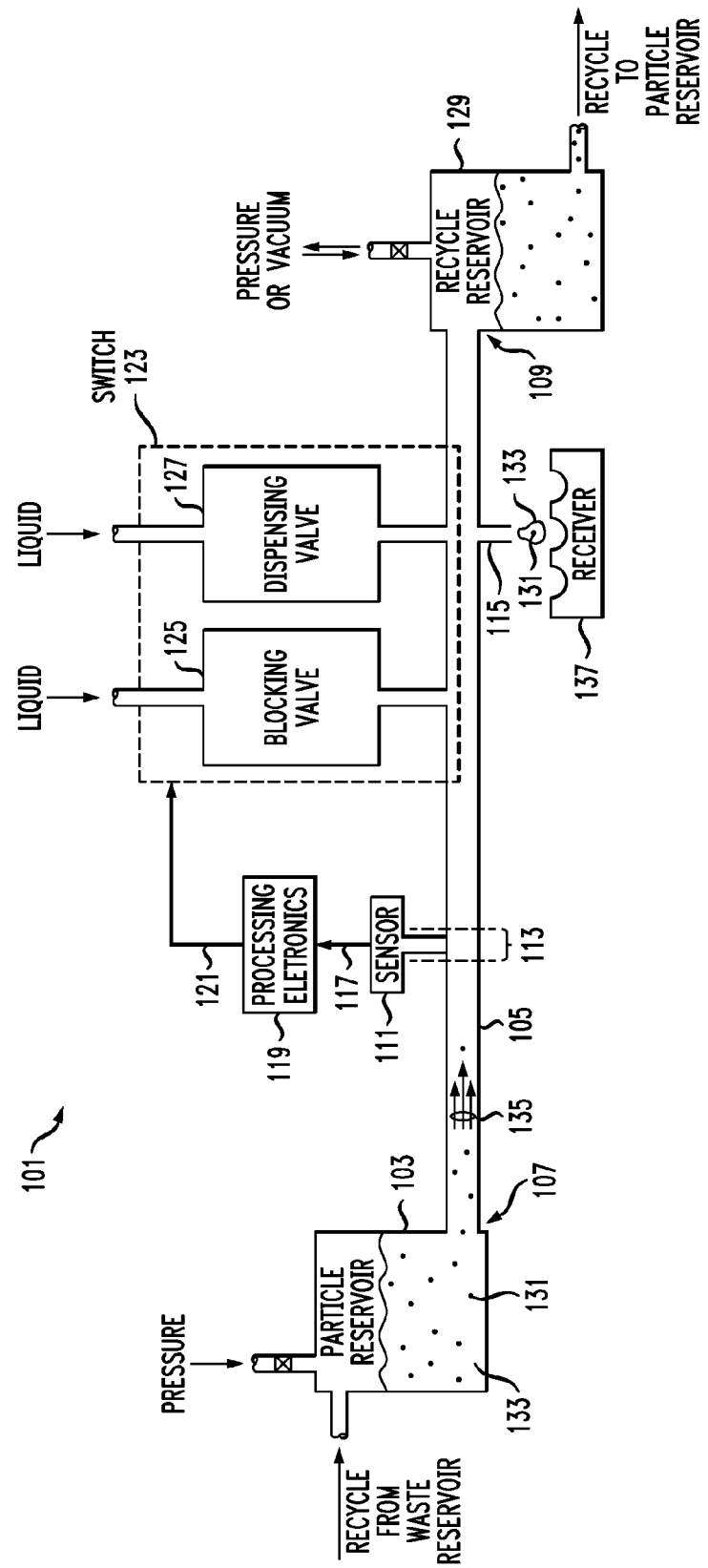

APPARATUS COMPRISING A PARTICLE SORTER/DISPENSER AND METHOD THEREFOR

STATEMENT OF RELATED APPLICATIONS

This application claims the benefit of U.S. Provisional Application Ser. No. 60/343,830, filed Oct. 25, 2001, entitled "Apparatus Comprising a Particle Sorter/Dispenser and Method Therefor," which is incorporated herein by reference.

FIELD OF THE INVENTION

The present invention relates generally to analyzing, sorting and dispensing particles from mixed populations.

BACKGROUND OF THE INVENTION

Many clinical and biological applications require that small particles (e.g., cells, multi-cellular organisms, microspheres, etc.) be sorted and dispensed. Small particles can be sorted and dispensed using a flow cytometer. In a typical flow cytometer, particles are introduced into a "sheath" fluid that flows into a vertical chamber or tube. The sheath fluid hydrodynamically focuses the particles toward the center of the chamber.

In some flow cytometers, the particles are electrostatically sorted. For example, in U.S. Pat. No. 6,248,590, the sheath fluid and suspended particles exit the chamber through a nozzle and free fall through open air. In free fall, the sheath fluid breaks up into droplets that contain the particles. The droplets pass through a sensing zone where the particles are interrogated by a sensor (e.g., optical sensor, etc.). Based on the results of the interrogation, the particles are sorted by diverting them (in either of two directions) or by not diverting them. The droplets are diverted by: (1) electrically charging them and (2) passing them through an electric field. The direction in which a charged droplet is diverted depends upon the charge (i.e., positive or negative) on the droplet. A neutral (i.e., uncharged) droplet falls un-diverted through the electric field. Vessels (e.g., multi-well plates, etc.) that are appropriately positioned below the chamber receive the diverted and un-diverted droplets.

In some other flow cytometers, the particles are pneumatically sorted. For example, in PCT Published Patent Application WO/00/11449, particles that are hydrodynamically-focused by the sheath fluid pass, one-by-one, through a sensing zone that is located within the vertical chamber. There, the particles are interrogated by a sensor. After interrogation, the sheath fluid and particles exit the chamber into open air. A desirable particle, as identified by the sensor and processing electronics, falls undisturbed (within a droplet) to an underlying receiver. In contrast, when undesirable particles are detected, an electrically-operated valve introduces a flow of compressed gas into the falling drops of sheath fluid thereby changing the path of the free-falling sheath fluid and undesirable particles. The diverted fluid and particles are collected in a waste reservoir and recycled, as appropriate.

These electrostatic and pneumatic flow cytometers suffer from a variety of drawbacks. One drawback is the need for very accurate timing. In particular, to sort particles, the particle-containing sheath fluid must be diverted—by electrostatics or a blast of gas—at a precise time after a particle is detected. Since the time delay is premised on a specific set of conditions (e.g., flow rate, temperature, flow pattern, etc.), these conditions must be maintained for accurate operation. Consequently, these systems require frequent re-calibration.

Another drawback of many prior art flow cytometers is that they are open systems. That is, the sheath fluid and particles are typically expelled into the ambient environment (e.g., air, etc.) before they are sorted. This approach results in a number of processing inefficiencies including slow response time, solvent loss due to evaporation and, to the extent that particles and/or associated moieties (e.g., chemical species attached to the particles, etc.) are oxygen sensitive, degradation.

SUMMARY OF THE INVENTION

The present invention provides a particle sorter/dispenser and method that avoids some of the drawbacks of the prior art.

In a particle sorter/dispenser in accordance with the illustrative embodiment, the sorting/dispensing portion of the system has a non-vertical, and preferably horizontal orientation. Furthermore, the sorting/dispensing portion of the system is substantially liquid full wherein particles are conducted through the particle sorter/dispenser suspended in a liquid. The speed of the particles through the system is, therefore, controllable. Consequently, the timing issues (e.g., when to divert a particle) that arise in prior-art flow cytometers are far less problematic in a particle sorter/dispenser in accordance with the illustrative embodiment of the present invention. In addition, the processing inefficiencies associated with the open configurations of prior art flow cytometers do not plague the illustrative particle dispenser/sorter described herein.

Some variations of a particle sorter/dispenser in accordance with the illustrative embodiment of the present invention include a particle reservoir that feeds a particle-containing liquid to a conduit. The conduit includes a sensing zone wherein the liquid-suspended particles are interrogated by a sensor. A dispensing orifice, through which particles are selectively dispensed to an underlying receiver, is disposed downstream of the sensing zone.

Data from the sensor is received by processing electronics. The processing electronics analyzes the sensor data, decides whether or not to dispense a particle, and generates a signal that is indicative of the decision. The signal is received by a switch. The switch controls whether or not a given particle is dispensed through the dispensing orifice. Particles that are not dispensed are flowed past the dispensing orifice to a recycle reservoir that depends from the downstream end of the conduit.

In some variations of the illustrative embodiment, the switch has two valves—a blocking valve and a dispensing valve. In some other variations, the switch has only one valve—the dispensing valve. Regarding the two-valve switch, the blocking valve is disposed downstream of the sensing zone and the dispensing valve is disposed downstream of the blocking valve and proximal to the dispensing orifice. Each valve independently controls a flow of liquid into the conduit. The liquid that is flowed through the valves is at a higher pressure than the particle-containing liquid already flowing through the conduit. Consequently, the liquid that is flowed through the valves into the conduit controls the flow of the particle-containing liquid that is already present in the conduit.

In further detail, when a desirable particle is detected, the blocking valve is opened. A relatively higher-pressure flow of liquid from the blocking valve enters the conduit downstream of the sensor and forms a curtain or barrier that the relatively lower-pressure particle-containing liquid cannot penetrate. As a consequence, any particle-containing liquid that has not progressed to the blocking valve is prevented from advancing beyond that point in the conduit.

Shortly after the blocking valve is opened, the dispensing valve is opened so that a relatively higher-pressure flow of liquid is introduced into conduit near the dispensing orifice. The liquid that enters the conduit through the dispensing valve is pressure controlled. The pressure is set so that the flow streamlines of the liquid control or occupy some but not all of the cross section of the dispensing orifice.

The flow of liquid through the blocking valve and the dispensing valve creates a high-pressure region in the conduit. Particles and liquid that are upstream of the blocking valve and/or downstream of the blocking valve cannot enter the high-pressure region and, consequently, will not be dispensed. Any particles downstream of the blocking valve and upstream of the dispensing valve (i.e., within the high-pressure region) are channeled, along with the higher-pressure liquid, through the dispensing orifice to a receiver.

In some variations of a particle sorter/dispenser in accordance with the illustrative embodiment, a portion of the conduit is configured as a venturi. The blocking and dispensing valves are advantageously located in the throat of the venturi. In some variations, the dispensing valve is located directly across from the open dispensing orifice in a "cross-venturi" arrangement. As a consequence of the pressure profile through the venturi, the particle-carrying flow is able to bypass the open dispensing orifice without exiting (when the dispensing valve is closed). When the dispensing valve is opened, the relatively higher-pressure liquid flowing into the venturi creates flow streamlines that lead across the venturi to the dispensing orifice. A particle in that region of the venturi is channeled by such flow streamlines through the dispensing orifice. This cross-venturi arrangement establishes very stable regions of flow, both when the dispensing valve is closed (i.e., the particle bypasses the dispensing orifice) and when the dispensing valve is open (i.e., the particle dispenses through the orifice). Furthermore, the flows are quick to re-establish after valve opening or closing.

A method in accordance with the illustrative embodiment of the present invention includes:

flowing particles along a first path in a first liquid;
detecting at least one of the particles;
flowing, during a first period of time that begins after the one particle is detected, a second liquid into the first liquid at a pressure that is sufficient to stop particles, other than the one particle, from flowing; and
dispensing the one particle by causing it to deviate from the first path.

BRIEF DESCRIPTION OF THE DRAWINGS

FIG. 1 depicts a particle sorter/dispenser in accordance with the illustrative embodiment of the present invention.

DETAILED DESCRIPTION

Figure 2A:
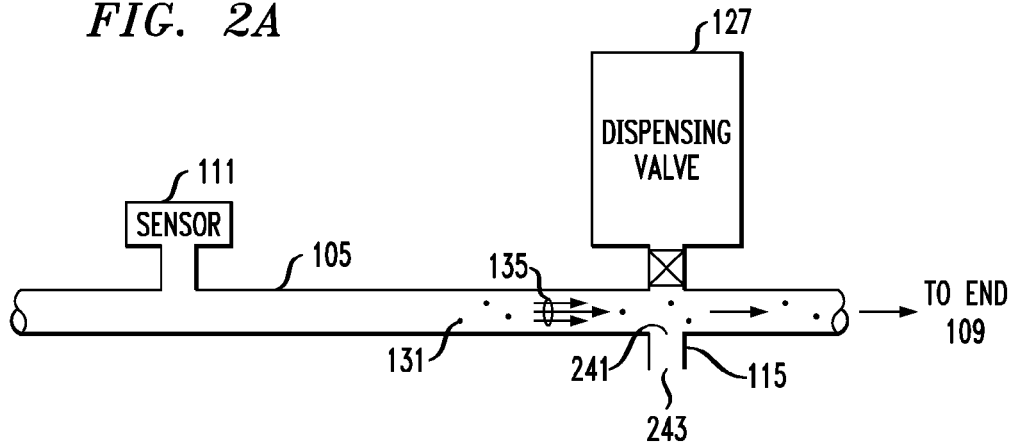
FIGS. 2A–2C depict flow patterns in a portion of the particle sorter/dispenser of FIG. 1 as a function of switch operation for a switch having a single valve.

FIG. 1 depicts particle sorter/dispenser 101 in accordance with the illustrative embodiment of the present invention. Particle sorter/dispenser 101 includes particle reservoir 103, conduit 105, sensor 111, dispensing orifice 115, processing electronics 119, switch 123, and recycle reservoir 129, arranged and interrelated as shown.

As used in this specification, the term "particle" includes, without limitation, biological cells (c.a., 5 to 30 microns in diameter), multi-cellular organisms, such as nematodes, etc. (c.a., 500 to 1000 microns) and micro-spheres, as are commonly used for combinatorial chemistry (c.a., 200 to 450 microns in diameter). Notwithstanding the definition of particle that is provided above, there is substantially no upper limit on the size of particles that can be sorted and dispensed using particle sorter/dispenser 101. That is, a very large particle can be sorted and dispensed via an appropriately-sized version of particle sorter/dispenser 101. The lower limit on particle size is dependent on the sensitivity of the detection method (i.e., extinction, fluorescence, light scattering, etc.) and the detector. With appropriate detection equipment, it is expected that particles as small as about 1 micron can be detected.

In the illustrative embodiment, particle reservoir 103 supplies particles 131 for particle sorter/dispenser 101. The particles are suspended in a liquid so that they can be flowed through conduit 105. Particle reservoir 103 is advantageously pressure controlled. In some embodiments, mixing action is provided, in known fashion, within particle reservoir 103 to distribute particles 131 within the liquid.

Upstream end 107 of conduit 105 receives flow 135 of particles 131 and liquid 133 (collectively, "particle-containing liquid 133") from particle reservoir 103. Particles 131 that are flowing through conduit 105 are interrogated by sensor 111 in sensing zone 113, which is located downstream of upstream end 107. Sensor 111, which is described in more detail later in this specification, is advantageously capable of obtaining data that is indicative of the size of particles 131 and/or indicative of other particle characteristics that are deemed to be important. Sensor 111 is also capable of generating signal 117 that is representative of the acquired data.

Processing electronics 119, described in more detail later in this specification, receives signal 117 from sensor 111 and analyzes the data carried by signal 117. The data might indicate, for example, that an interrogated particle meets specification such that it should be dispensed from dispensing orifice 115 to receiver 137. Alternatively, the data might indicate that an interrogated particle does not meet specification and, consequently, should not be dispensed.

Processing electronics 119 reaches a decision as to the disposition of a given particle (e.g., dispense or do not dispense, etc.) based on the data, and generates signal 121 that is indicative of the decision. Signal 121 is then transmitted to switch 123.

Responsive to signal 121, switch 123 affects flow conditions within conduit 105. In particular, in one state of switch 123, flow conditions are affected in such a way that at least one particle 131 is dispensed to receiver 137 through dispensing orifice 115. For many applications, it is advantageous to dispense only one particle 131 at a time, and particle sorter/dispenser 101 can be operated to do this. In another state of switch 123, flow conditions are affected in such a way that flow 135 of particle-containing liquid 133 bypasses dispensing orifice 115, exits conduit 115 at downstream end 109, and flows into recycle reservoir 129.

In some variations of the illustrative embodiment, particle-containing liquid 133 in recycle reservoir 129 is recycled to particle reservoir 103. In some other variations of the illustrative embodiment, particle-containing liquid 133 is not recycled. Rather, when particle reservoir 103 is empty and recycle reservoir 129 is full, the reservoirs are removed from respective ends of conduit 105 and switched. That is, recycle reservoir 129 is engaged to upstream end 107 of conduit 105 while particle reservoir 103 is engaged to downstream end 109. Those skilled in the art will be able to make and use particle reservoir 103 and recycle reservoir 129 and/or to provide another source of particles 131 and liquid 133 for use in particle sorter/dispenser 101.

In summary, as a function of the operation of sensor 111, processing electronics 119 and switch 123, particle-containing liquid 133 that is received by conduit 105 is either:
(1) dispensed through dispensing orifice 115 and into receiver 137, or
(2) flowed past second end 109 of conduit 105 to recycle reservoir 129.

The physical configuration and operation of switch 123 is now described in detail. In some variations of the illustrative embodiment, such as the one depicted in FIG. 1, switch 123 includes two valves: blocking valve 125 and dispensing valve 127. In some other variations of the illustrative embodiment, switch 123 includes only one valve: dispensing valve 127. Valves 125 and 127 each (independently) control a flow of liquid into conduit 105. The liquid that is flowed through valve 125 can be the same as or different than the liquid that is flowed through valve 127. Furthermore, the liquid that is flowed through valves 125 and 127 can be the same as or different than liquid 133 in which particles 131 are suspended. Typically, a single liquid is used for all of these services. It will be appreciated that the liquid 133 within particle reservoir 103 should be inert or otherwise benign to particles 131 (and to any chemical species, etc., that are attached or otherwise associated with the particles). In some embodiments, the liquid that is flowed through dispensing valve 127 can be reactive. Thus, in addition to dispensing particles 131, particle sorter/dispenser 101 can dispense reactive liquid to receiver 137.

Figure 2B:
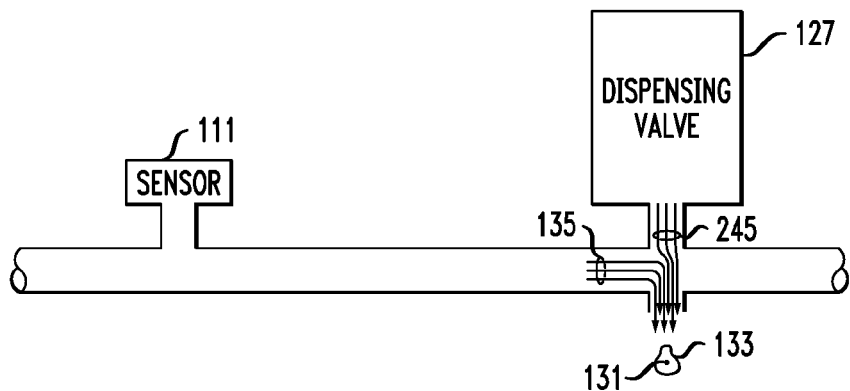
Figure 2C:
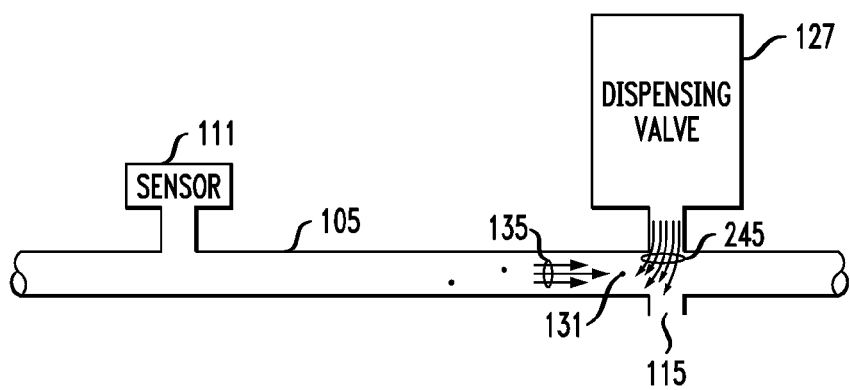

The flow of liquid through valves 125 and/or 127 affects or controls flow 135 of particle-containing liquid 133 through conduit 105. FIGS. 2A–2C illustrate how this occurs for a switch 123 having only one valve (i.e., dispensing valve 127). These Figures depict a portion of particle sorter/dispenser 101 that includes sensor 111, dispensing orifice 115, and dispensing valve 127. In the description that follows, it is assumed that valve 127 is operating in response to signal 121 from processing electronics 119 in the manner previously described.

FIG. 2A depicts switch 123 in a state in which particle 131 is not dispensed; rather, flow 135 bypasses dispensing orifice 115 and exits conduit 105 at downstream end 109. In this state, dispensing valve 127 is closed so that there is no flow of liquid into conduit 105 through the dispensing valve. Flow 135 bypasses dispensing orifice 115 in this state because the pressure in conduit 105 at inlet 241 of dispensing orifice 115 is less than the ambient pressure at outlet 243 of dispensing orifice 115. Advantageously, the pressure at inlet 241 is slightly less than the ambient pressure so that a very small amount of air is aspirated into conduit 105 through dispensing orifice 115. This ensures that there will be no leakage of liquid 133 (and particles 131) through dispensing orifice 115.

FIG. 2B depicts switch 123 in a state in which particle 131 and some accompanying liquid 133 is dispensed through dispensing orifice 115. In this state of the switch, dispensing valve 127 is open so that flow 245 of liquid is introduced into conduit 105 near dispensing orifice 115. The pressure of flow 245 is controlled so that the flow pattern depicted in FIG. 2B develops. Specifically, flow 245 is directed toward dispensing orifice 115 such that the streamlines of relatively higher-pressure flow 245 control some but not all of the flow through the orifice. In other words, a path through dispensing orifice 115 remains for relatively lower-pressure flow 135. Particle 131 and some accompanying liquid 133) flowing through conduit 105 is therefore conducted, along with flow 245, through dispensing orifice 115.

In one mode of operation, dispensing valve 127 opens after a specific time delay to dispense particle 131 and then rapidly closes to ensure that only the desired particle(s) is dispensed. The valve timing, which is described in more detail later in this specification, is based on particle transit time from sensing region 113 to dispensing orifice 115. In another mode of operation, pressure is adjusted (reduced) through particle sorter/dispenser 101 to slow flow 135 of particles 131 such that valve timing is of decreased significance. In this mode of operation, it is advantageous to draw a partial vacuum on recycle reservoir 129 so that particle reservoir 103 can be operated at sub-atmospheric pressure.

FIG. 2C depicts switch 123 in a state in which flow 135 of particle-containing liquid 133 is stopped at a point upstream of dispensing orifice 115. In this state of the switch, dispensing valve 127 is open so that flow 245 of liquid is introduced into conduit 105 near dispensing orifice 115. The pressure of flow 245 is controlled so that the flow pattern depicted in FIG. 2C develops. In this flow pattern, the streamlines of flow 245 completely fill dispensing orifice 115 thereby forming a barrier or curtain through conduit 105 at the leading edge of dispensing orifice 115. Since (lower-pressure) flow 135 cannot penetrate the (higher-pressure) curtain, a particle 131 flowing through conduit 105 toward dispensing orifice 115 is stopped before it can dispense. The ability to stop a particle in this fashion is particularly advantageous for assays and other analysis work.

Figure 3A:
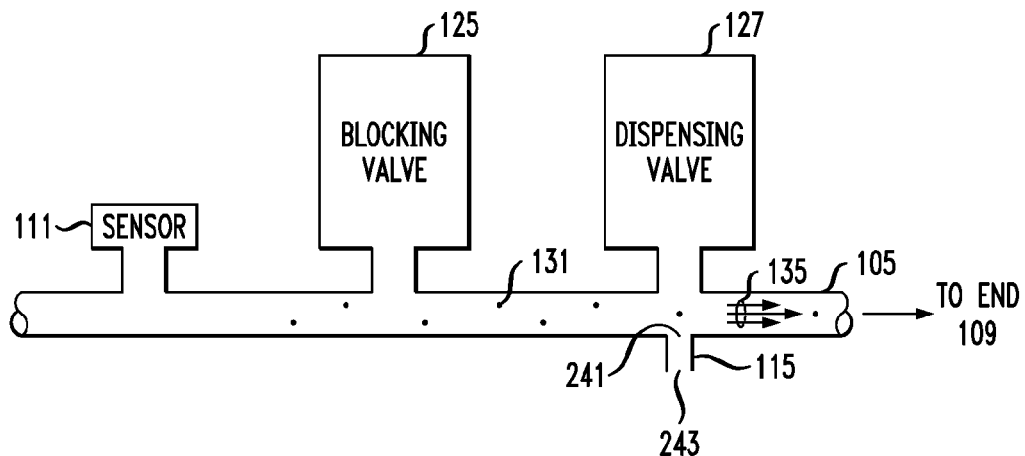
FIGS. 3A–3B depict flow patterns in a portion of the particle sorter/dispenser of FIG. 1 as a function of switch operation for a switch having two valves.
Figure 3B:
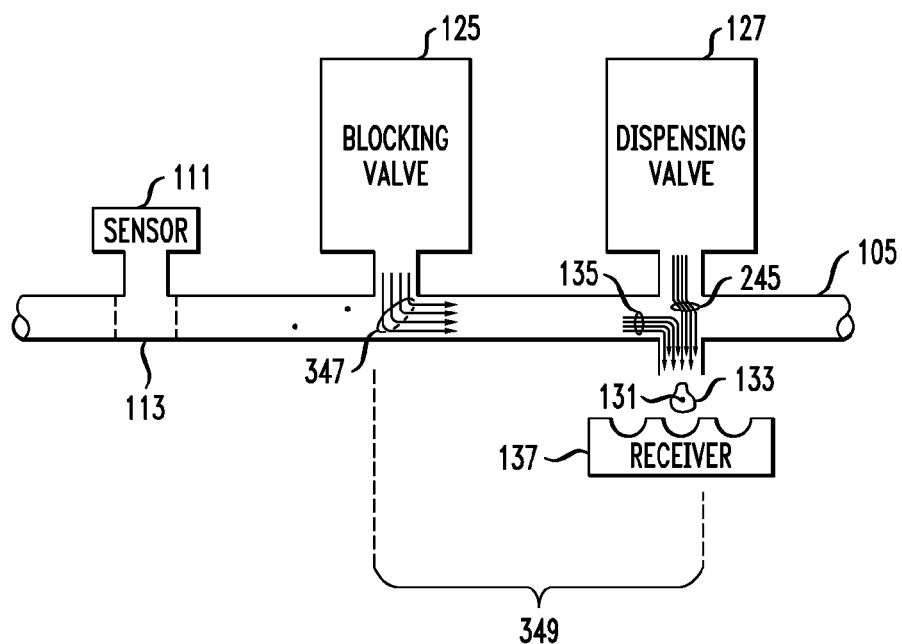

FIGS. 3A and 3B depict a way in which a switch 123 that has two valves (i.e., both blocking valve 125 and dispensing valve 127) affects or controls flow 135 in conduit 105. These Figures depict a portion of particle sorter/dispenser 101 that includes sensor 111, dispensing orifice 115, blocking valve 125 and dispensing valve 127. In the description that follows, it is assumed that valves 125 and 127 are operating in response to signal 121 from processing electronics 119 in the manner previously described.

FIG. 3A depicts switch 123 in a state in which particle 131 does not dispense. In this state, blocking valve 125 and dispensing valve 127 are closed so that there is no flow through these valves into conduit 105. Flow 135 bypasses dispensing orifice 115 and exits conduit 105 at downstream end 109. Flow 135 bypasses dispensing orifice 115 in this state because the pressure in conduit 105 at inlet 241 of dispensing orifice 115 is less than the ambient pressure at outlet 243 of dispensing orifice 115.

FIG. 3B depicts switch 123 in a state in which particle 131 and some accompanying liquid 133 is dispensed through dispensing orifice 115. As previously described, for a switch 123 that has a single valve (i.e., dispensing valve 127), the valve is closed shortly after opening (in one mode of operation) to prevent undesirable particles 131 from dispensing through dispensing orifice 115. But when switch 123 incorporates two valves (i.e., blocking valve 125 and dispensing valve 127), the flow of liquid through blocking valve 125, rather than the valve timing of dispensing valve 127, is advantageously used to prevent undesirable particles 131 from dispensing. This mode of operation is described below.

Assume that particle 131 is interrogated in sensing zone 113 and, based on analysis performed by processing electronics 119, it is determined that the particle should be dispensed. After a delay, during which time particle 131 flows from sensing zone 113 past blocking valve 125, the blocking valve is opened. Relatively higher-pressure flow 347 from blocking valve 125 enters conduit 105 and forms a curtain or barrier that the relatively lower-pressure flow 135 of particle-containing liquid 133 cannot penetrate. Consequently, any particle-containing liquid 133 that has not yet reached blocking valve 125 is prevented from advancing beyond that point in conduit 105.

Shortly after blocking valve 125 is opened, dispensing valve 127 is opened so that flow 245 of liquid is introduced into conduit 105 near dispensing orifice 115. The pressure of flow 245 is controlled so that the flow pattern depicted in FIG. 3B develops. Specifically, flow 245 is directed toward dispensing orifice 115 such that the streamlines of flow 245 control some but not all of the flow through the orifice. Any particles 131 downstream of blocking valve 125 and upstream of dispensing valve 127 are channeled, along with flow 245, through dispensing orifice 115 to receiver 137.

Flow 347 of liquid through valve 125 and flow 245 of liquid through valve 127 create high-pressure region 349. Particles 131 and liquid 133 that are upstream of valve 125 or downstream of valve 127 cannot enter high-pressure region 349 and, consequently, will not be dispensed. For this reason, rapid closure of dispensing valve 127 is not required to prevent undesirable particles from dispensing. Further description of valve timing is provided later in this specification.

For reliable and proper functioning of particle sorter/dispenser 101, a specific pressure profile is desirable, if not required, through conduit 105, especially in the region near dispensing orifice 115. In particular, (1) a lower than ambient pressure must be obtained at inlet 241 of dispensing orifice 115; and
(2) the pressure must increase downstream of dispensing orifice 115.

Regarding point (1), having low pressure at the inlet to dispensing orifice 115 ensures that particle-containing liquid 133 will simply bypass dispensing orifice 115, without leakage, when dispensing valve 127 is closed. Regarding point (2), the increase in pressure downstream of dispensing orifice 115 ensures that there is enough pressure to push flow 135 of particle-containing fluid 133 past downstream end 109 and into recycle reservoir 129.

The inventors recognized that the desired pressure profile can be obtained by the well-known venturi configuration. To that end, in some variations of particle sorter/dispenser 101 in accordance with the illustrative embodiment, a portion of conduit 105 is configured as a venturi.

Figure 4:
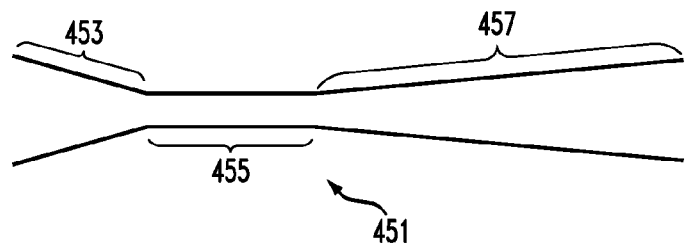
FIG. 4 depicts a conventional venturi.

A conventional venturi 451 is depicted in FIG. 4. Venturi 451 comprises convergent region 453, throat 455, and divergent region 457. Convergent region 453 typically has an included angle of about 21° and divergent region 457 has an included angle of about 7 to 8°.

Figure 5:
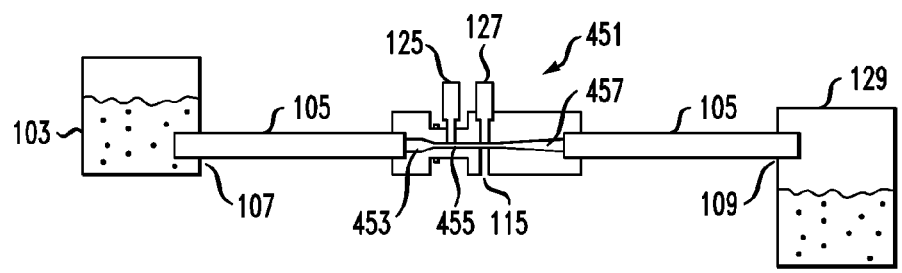
FIG. 5 depicts a particle sorter/dispenser in accordance with the illustrative embodiment of the present invention, wherein the particle sorter/dispenser includes a venturi.

As depicted in FIG. 5, venturi 451 is located downstream of upstream end 107 and upstream of downstream end 109 of conduit 105. In a variation of particle sorter/dispenser 101 depicted in FIG. 6, sensing zone 113, blocking valve 125 and dispensing valve 127 are disposed within (or depend from) throat 455 of venturi 451. In some other embodiments, sensing zone 113 is disposed upstream of throat 455, such as in convergent region 453. It is, however, advantageous to locate sensing zone 113 in throat 455 since the cross section for flow is narrower in throat 455 than in convergent region 453. This reduces the required coverage area of sensor 111.

Figure 6:
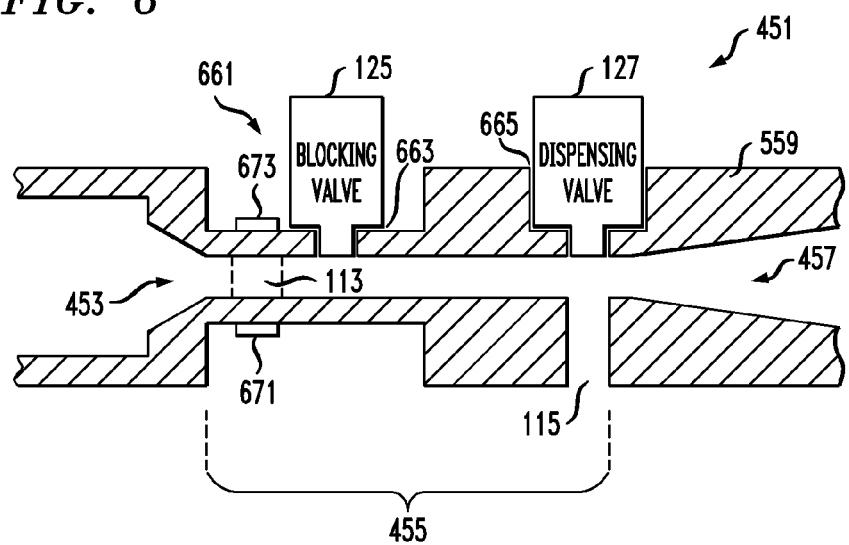
FIG. 6 depicts a venturi configured for use in conjunction with the illustrative embodiment of the present invention.

In some variations, such as the one depicted in FIGS. 5 and 6, venturi 451 is formed within material 559, which can be, without limitation, polycarbonate or other materials. Material 559 must be inert to the flowing liquids and particles, and should be suitably stable and robust for machining, etc., to form holes, such as for dispensing orifice 115 and holes 663 and 665 that receive valves 125 and 127.

Furthermore, material 559 is advantageously visually transparent so that conditions within venturi 451 can be observed. It is particularly important that material 559 is permeable to electromagnetic radiation at the operating wavelength of sensor 111 so that particles 131 flowing through sensing zone 113 can be interrogated (for variations in which sensor 111 is located on the exterior of venturi 451). For optical sensors, material 559 can be opaque as long as an optical path is provided between sensor 111 and the interior of conduit 105 at sensing zone 113. This optical path can be provided, for example, by inserting two lenses (not depicted), such as collimating lenses, through material 559 at diametrically-opposed regions of sensing zone 113. One of the lens places emitter 671 (of sensor 111) in optical communication with the interior of conduit 105, and the other lens places detector 673 (of sensor 111) in optical communication with the interior of conduit 105. In fact, for optical sensing, regardless of whether or not material 559 is opaque, collimating lenses are advantageously inserted through material 559 to minimize optical aberrations, thereby improving the accuracy of particle detection.

In the variation depicted in FIG. 6, material 559 is thinned at region 661 surrounding a portion of throat 455. This allows emitter 671 and detector 673 to be situated closer to the liquid flow within venturi 451. In the illustration, blocking valve 125 is also disposed within thinned region 661. In some other variations (not depicted), sensor 111 is a fiber-optic sensor wherein a first optical fiber is attached to the emitter and a second optical fiber is attached to the detector. Two very small, diametrically-opposed holes are formed through material 559. The fiber that is attached to the emitter is inserted into one of the holes, and the fiber that is attached to the detector is inserted into the other of the holes. In these variations, region 551 is not included.

To simplify issues relating to the positioning of emitter 671 and detector 673, in another variation (not shown) of particle sorter/detector 101, venturi 451 is formed within thin walled tubing that is shaped into the venturi configuration.

In some variations of particle sorter/detector 101, the surfaces of conduit 105 facing emitter 671 and detector 673 of sensor 111 are advantageously flat and parallel to one another, rather than curved as for a typical cylindrical conduit. Flat surfaces improve the accuracy of (optical) particle detection. In practice, flat, parallel surfaces can be provided by inserting, within sensing zone 113, a capillary tube having a rectangular cross section. Alternatively, the portion of the conduit at sensing zone 113 (e.g., throat 455) can itself be formed with a rectangular cross section.

With regard to sensor 111, any one of a variety of different types of sensors (e.g., optical, electromagnetic, etc.) is suitable for use in conjunction with illustrative particle sorter/dispenser 101. For example, as to optical sensors, a simple position sensor having emitter 671 and photodetector 673 operating at about 850 nm wavelength is suitable. Alternatively, fiber optic sensors, as described above, can be used. Regardless of its specific configuration, sensor 111, in conjunction with suitable processing electronics, is advantageously capable of determining the size of particles 131 and is further advantageously capable of determining whether two or more particles are stuck together. Those skilled in the art will be able to suitably select and operate sensor 111.

For particle sorter/dispenser 101 that is suitable for sorting/dispensing particles in the 200–1000 micron size range, the flow rate will be such that action should be taken (i.e., a valve should be opened) within about 10 milliseconds after a particle is detected. Consequently, processing electronics 119 is advantageously a suitably-programmed, fast, real-time processor that runs independently of a PC operating system (normally the main cause of delays in processing data). A suitable microprocessor is the DAP4000/12 from MicroStar Laboratories of Bellevue, Wash. The processor collects and analyzes data, and generates a digital or analog signal as a result of the data analysis.

With regard to dispensing orifice 115, in some variations of the illustrative embodiment, dispensing orifice 115 is simply a hole leading from throat 455 to the ambient environment. In some other variations (not depicted) dispensing orifice 115 is implemented as nozzle.

To cleanly dispense particles 131 to underlying receiver 137, dispensing orifice 115 is advantageously vertical. For ease of fabrication, dispensing orifice 115 is formed so that it is perpendicular to throat 455. Consequently, venturi 451 will be horizontal during operation. In some other variations of the illustrative embodiment, venturi 451 is disposed in a non-vertical (but not horizontal) orientation. In such a variation, dispensing orifice 115 is advantageously not perpendicular to throat 455. Specifically, if venturi 451 is tilted by α degrees relative to the horizontal, the included angle between dispensing orifice 115 and throat 455 is 90°–α degrees.

As previously described, the operation of switch 123 is dependent on the results of data analysis and decision-making performed by processing electronics 119. Further description concerning data analysis, decision-making and valve timing is presented in conjunction with FIGS. 7–9. These FIGS. and the accompanying description pertain to a switch 123 having both blocking valve 125 and dispensing valve 127. It will be clear to those skilled in the art how to modify this teaching for a switch 123 having a dispensing valve 127 only.

Figure 7:
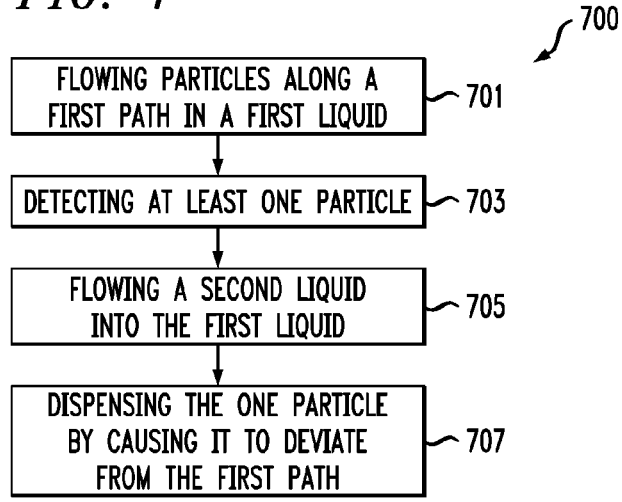
FIG. 7 depicts a method for particle sorting and dispensing in accordance with the illustrative embodiment of the present invention.
Figure 8:
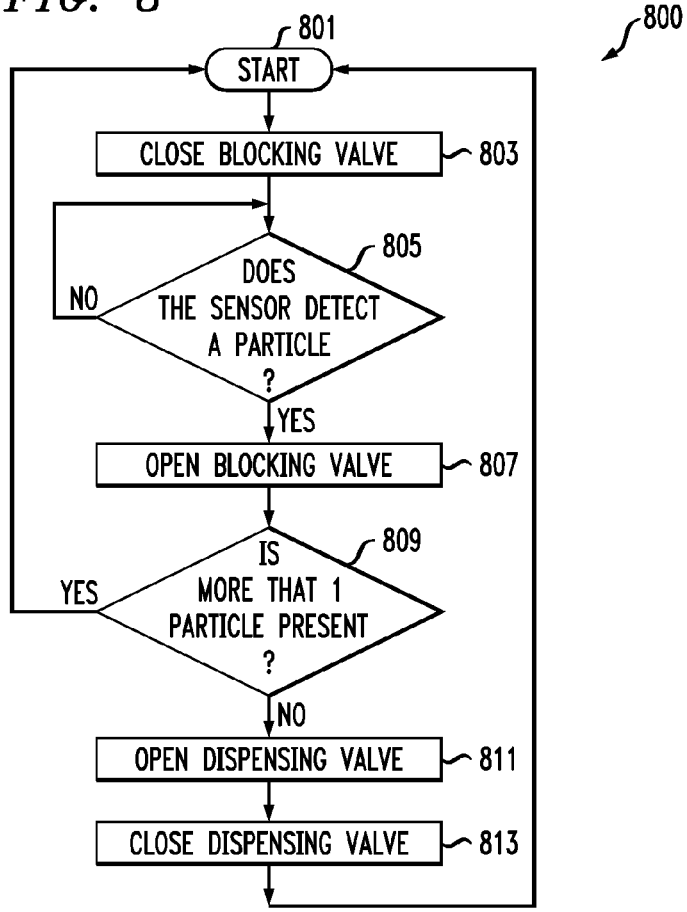
FIG. 8 depicts a method for operating a particle sorter/dispenser in accordance with the illustrative embodiment of the present invention.
Figure 9:
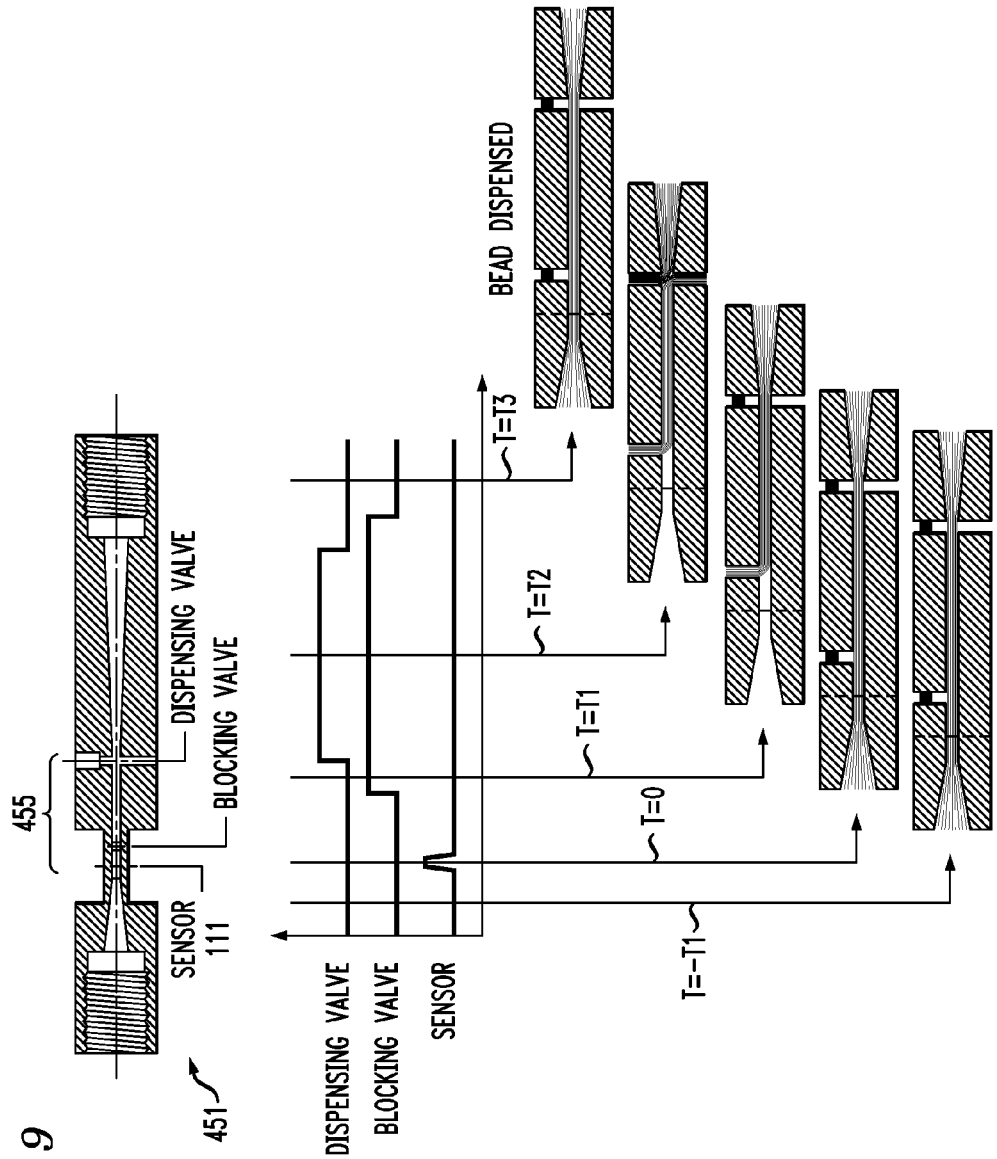
FIG. 9 depicts a timing diagram for a switch in particle sorter/dispenser of FIG. 1.

FIG. 7 depicts a method 700 for particle sorting and dispensing in accordance with the illustrative embodiment of the present invention. FIG. 8 depicts a method 800 by which method 700 is performed. In other words, FIG. 8 depicts a method for operating particle sorter/dispenser 101 in accordance with the illustrative embodiment of the present invention. And FIG. 9 depicts a timing diagram showing sensor operation and valve timing for practicing methods 700 and 800.

In accordance with operation 701 of method 700, particles are flowed along a first path in a first liquid. The path is advantageously non-vertical, and, more preferably, the path is horizontal. With regard to method 800, operation 701 is implemented by operation 803: closing blocking valve 125 (if it is open from a previous sorting/dispensing operation). As previously described, when blocking valve 125 is open, flow 347 (FIG. 3B) prevents flow 135 of particle-containing liquid 133 from advancing through conduit 105. In the timing diagram depicted in FIG. 9, valve 125 is closed as a final event in the sorting/dispensing operation. This occurs at T=T3. A particle is depicted flowing toward sensing zone 113 at T=−T1.

In operation 703 of method 700, at least one of the flowing particles is detected. Particle detection is depicted as a spike in the detector trace shown in FIG. 9. Particle detection occurs in sensing zone 113 at T=0. With regard to the operation of sensor 111, the detection operation involves acquiring a signal having a certain minimum strength and observing the signal for a certain period of time. If the signal is observed for less than the expected period of time, it might indicate that the particle is a fragment of a greater whole, such as, for example, a fragment of a micro-sphere. If the signal is observed for too long a period of time, this might indicate that two or more particles are stuck together.

Particle detection is shown as operation 805 of method 800. Valve 125 remains closed until a desirable particle is detected. Since, at this point in the method, valve 125 and valve 127 are closed, particle-containing liquid bypasses dispensing orifice 115 and is received by recycle reservoir 129.

In accordance with operation 705 of method 700, after a desirable particle is detected, a second liquid is flowed into the first liquid at a pressure that is sufficient to stop particles other than the desirable particle from flowing. This operation is effected in method 800 by opening blocking valve 125 at operation 807. In the timing diagram depicted in FIG. 9, valve 125 opens at T=T1. Timing is dependent, of course, on flow conditions. For the particle sorter/dispenser 101 described below, and with flows on the order of 0.1 milliliter/second, valve 125 opens at about 1–2 milliseconds after detection. The corresponding view of particle sorter/dispenser 101 shows liquid flowing through valve 125 into conduit 105. As previously described, this flow prevents any particle-containing liquid that is upstream of valve 125 from proceeding through conduit 105. Valve 125 is advantageously opened immediately upon detecting a particle.

Delays are inherent in the particle sorting/dispensing process (e.g., sensor response time, valve response time, etc.). Therefore, when a single particle is to be dispensed, no particle should trail or lead a desired particle so closely that it cannot be physically segregated (i.e., by the action of valves 125 and 127) from the desired particle. Consequently, a time interval before and after the desired particle is detected is advantageously checked for the presence of other particles. In accordance with operation 809 of method 800, if particles are present during those time intervals, valve 127 remains closed so that none of the particles, including the desired particle, dispense.

In operation 707, the desirable particle is dispensed. In accordance with operation 811 of method 800, operation 707 is effected by opening valve 127 to cause relatively high-pressure liquid to flow into conduit 105 toward dispensing orifice 115. This flow conducts the desirable particle through dispensing orifice 115. In the timing diagram depicted in FIG. 9, valve 127 opens at T=T2. For the aforementioned flow conditions and physical description provided below, valve 127 opens at a time that is about 1–3 milliseconds after T1. After valve 127 has been open for a sufficient amount of time to dispense the desirable particle, valve 127 is closed, as per operation 813. In the timing diagram depicted in FIG. 9, valve 127 closes at T=T3. For the aforementioned flow conditions and physical description of an illustrative particle sorter/dispenser provided below, valve 127 is fully closed at a time that is about 13–17 milliseconds after T1. Valve opening and closing takes about 2 millisecs.

ILLUSTRATIVE PARTICLE SORTER/DISPENSER

The size and operating conditions of particle sorter/dispenser 101 can be determined as follows. As a "rule-of-thumb," the diameter of the conduit at sensing zone 113 is advantageously less than about five times the size (e.g., diameter, etc.) of particles 131. With the diameter set, the pressure balance is established in conjunction with establishing the flow rate. For a venturi configuration, the flow rate is adjusted to provide a small amount of aspiration through dispensing orifice 115 within throat 455. This ensures that as long as dispensing valve 127 is closed, particles flowing through throat 455 will bypass dispensing orifice 115. This provides the minimum flow rate. The flow rate of particle-carrying liquid 133 is limited to a rate that ensures that sensor 111 is able to detect particle 131. Of course, as flow rate increases above the minimum described above, the amount of fluid aspirated by dispensing orifice 115 increases. At some point, the amount of fluid aspirated might become unacceptably high. Consequently, in some cases, the flow rate might be limited by the system's tolerance to aspirated fluid.

A particle sorter/dispenser configured as described above was assembled and operated to reliably sort particles. Details of the particle sorter/dispenser operation follow:

| | |
|---|---|
| Particles: | microspheres, 200 microns average diameter |
| Liquid: | 50:50 isopropyl alcohol:water |
| Particle reservoir pressure: | 1.5 psig |
| Recycle reservoir pressure: | 0 psig |
| Throat diameter: | 0.024 inches |
| Dispensing orifice diameter: | 0.024 inches |
| Blocking valve size: | 0.05 inches |
| Dispensing valve size: | 0.05 inches |
| Pressure of Liquid through valves: | 25–30 psig |
| Flow rate though throat: | 0.1–1 milliliter per second |

We claim:

1. An apparatus comprising:
a conduit, wherein said conduit receives a flow of a first liquid that contains particles, and wherein said conduit comprises a venturi with a throat, wherein the flow of the first liquid in the throat has a pressure lower than ambient;
a sensor that detects said particles in a sensing zone of said conduit;
a dispensing orifice, wherein said dispensing orifice is disposed in said throat of said venturi; and
a switch, wherein responsive to said sensor detecting a particle, said switch causes the pressure inside the throat to increase so that the detected particle is despensed through the dispensing orifice rather that flowing past the orfice.

2. The apparatus of claim 1 wherein said switch comprises an dispensing valve that is disposed downstream of said sensing zone and proximal to said dispensing orifice.

3. The apparatus of claim 2 wherein, when said dispensing valve opens to a first position, a second liquid flows into said conduit at a pressure that establishes a flow pattern in said conduit that directs said at least one particle to flow through said dispensing orifice.

4. The apparatus of claim 2 wherein, when said dispensing valve opens to a second position, a second liquid flows into said conduit at a pressure that establishes a flow pattern in said conduit that prevents said at least one particle from reaching said dispensing orifice.

5. The apparatus of claim 2 wherein said switch further comprises an blocking valve that is disposed downstream of said sensing zone and upstream of said dispensing valve.

6. The apparatus of claim 5 wherein, when open, said blocking valve causes a third liquid to flow into said conduit at a pressure that establishes a flow pattern in said conduit that prevents the flow of said first liquid and said particles from flowing past said blocking valve.

7. The apparatus of claim 1 wherein said sensing zone is in said throat.

8. The apparatus of claim 1 wherein said venturi is disposed in a non-vertical orientation.

9. An apparatus comprising:
a venturi, said venturi having a convergent region, a throat, and a divergent region;
a sensor that detects particles in a sensing zone in said venturi, wherein said particles flow in a first liquid that enters said venturi via said convergent region and wherein the throat has a pressure lower than ambient;
a dispensing orifice that dispenses some of said particles that are detected in said venturi by said sensor, wherein said dispensing orifice is disposed downstream of said sensing zone and in said throat of said venturi; and
a dispensing valve that is disposed in diametrically-opposed relation to said dispensing orifice, wherein said dispensing valve controls the flow of a second liquid into said venturi, and wherein the flow of said second liquid causes an increase in the pressure in the throat of the venturi so that at least one of said particles that are detected in said sensing zone is dispensed through said dispensing orfice rather than flowing past the orfice.

10. The apparatus of claim 9 wherein said dispensing orifice dispenses said particles from said throat and said dispensing valve delivers the flow of said second liquid into said throat.

11. The apparatus of claim 9, further comprising a blocking valve that is located downstream of said sensing zone, upstream of said dispensing valve and upstream of said dispensing orifice, wherein said blocking valve controls the flow of a third liquid into said venturi.

12. The apparatus of claim 11 wherein the flow of said third liquid prevents said particles and said first liquid from flowing past said blocking valve toward said dispensing valve.

13. The apparatus of claim 9 wherein said sensor is an optical detector.

14. The apparatus of claim 9 wherein said venturi is disposed in a substantially horizontal orientation.

15. An apparatus comprising:
a conduit, wherein said conduit receives a flow of a first liquid that contains particles, and wherein said conduit comprises a venturi with a throat, wherein the flow of the first liquid in the throat has a pressure lower than ambient a sensor, wherein said sensor detects said particles in a sensing zone of said conduit;

a dispensing valve, wherein said dispensing valve delivers a flow of a second liquid into said throat of said venturi so as to increase the pressure in the throat; and a dispensing orifice that dispenses at least one of said particles when said second liquid is delivered into said throat due to the pressure increase, wherein said dispensing orifice is disposed in said throat, and further wherein said dispensing valve and said dispensing orifice are disposed downstream of said sensing zone and at the same axial position along said throat.

16. The apparatus of claim 15 further comprising a reservoir, wherein said reservoir is in fluidic communication with said conduit and is disposed downstream of said dispensing orifice, and further wherein said reservoir is operated under partial vacuum.

17. The apparatus of claim 15 wherein said dispensing valve and said dispensing orifice are diametrically opposed to one another.

18. The apparatus of claim 15 wherein said sensing zone is in said throat of said venturi.

19. The apparatus of claim 15 further comprising a blocking valve, wherein said blocking valve is disposed upstream of said dispensing valve, and further wherein said blocking valve controls the flow of a third liquid into said conduit.

* * * * *